United States Patent
Arseneau

(10) Patent No.: US 7,355,167 B2
(45) Date of Patent: Apr. 8, 2008

(54) AFTERGLOW DC-OFFSET CALIBRATION IN A NUCLEAR IMAGING SYSTEM

(75) Inventor: Roger E. Arseneau, Buffalo Grove, IL (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 0 days.

(21) Appl. No.: 11/728,414

(22) Filed: Mar. 26, 2007

(65) Prior Publication Data

US 2007/0170357 A1 Jul. 26, 2007

Related U.S. Application Data

(62) Division of application No. 11/239,270, filed on Sep. 29, 2005, now Pat. No. 7,211,800.

(51) Int. Cl.
*G12B 13/00* (2006.01)

(52) U.S. Cl. .................................................. 250/252.1

(58) Field of Classification Search ............. 250/252.1, 250/363.09
See application file for complete search history.

(56) References Cited

U.S. PATENT DOCUMENTS

| | | | | |
|---|---|---|---|---|
| 6,403,960 | B1* | 6/2002 | Wellnitz et al. | 250/363.09 |
| 2004/0036025 | A1* | 2/2004 | Wong et al. | 250/363.09 |

* cited by examiner

*Primary Examiner*—David Porta
*Assistant Examiner*—Marcus H Taningco

(57) ABSTRACT

Method and system are provided for calibrating a nuclear medical imaging apparatus for DC shift caused by gamma event afterglow pulses. Detector responses to weak and to high count rate radiation sources are compared with each other, and a zero correction value is incremented until the detector response is the same for the weak source and the high count rate source. The zero correction value is then stored as a static zero correction value, which multiplies a dynamic zero correction value obtained just prior to the occurrence of a gamma event, in order to remove the effects of DC shifts from the output energy signal Esum.

4 Claims, 3 Drawing Sheets

US 7,355,167 B2

AFTERGLOW DC-OFFSET CALIBRATION IN A NUCLEAR IMAGING SYSTEM

CROSS-REFERENCE TO RELATED APPLICATION AND CLAIM FOR PRIORITY

This application is a divisional of and claims priority from application Ser. No. 11/239,270 filed Sep. 29, 2005 now U.S. Pat. No. 7,211,800, under 35 U.S.C. § 120.

BACKGROUND OF THE INVENTION

1. Field of the Invention

The present invention generally relates to nuclear medicine, and systems for obtaining nuclear medicine images of a patient's body organs of interest. In particular, the present invention relates to a novel method and system for more accurately detecting the occurrence of valid scintillation events.

2. Description of the Background Art

Nuclear medicine is a unique medical specialty wherein radiation is used to acquire images that show the function and anatomy of organs, bones or tissues of the body. Radiopharmaceuticals are introduced into the body, either by injection or ingestion, and are attracted to specific organs, bones or tissues of interest. Such radiopharmaceuticals produce gamma photon emissions that emanate from the body. One or more detectors are used to detect the emitted gamma photons, and the information collected from the detector(s) is processed to calculate the position of origin of the emitted photon from the source (i.e., the body organ or tissue under study). The accumulation of a large number of emitted gamma positions allows an image of the organ or tissue under study to be displayed.

Emitted gamma photons are typically detected by placing a scintillator over the region of interest. Such scintillators are conventionally made of crystalline material such as NaI (Tl), which interacts with absorbed gamma photons to produce flashes of visible light. The light photons emitted from the scintillator crystal are in turn detected by photosensor devices that are optically coupled to the scintillator crystal, such as photomultiplier tubes. The photosensor devices convert the received light photons into electrical pulses whose magnitude corresponds to the amount of light photons impinging on the photosensitive area of the photosensor device.

Not all gamma interactions in a scintillator crystal can be used to construct an image of the target object. Some of the interactions may be caused by gamma photons that were scattered or changed in direction of travel from their original trajectory. Thus, one conventional method that has been used to test the validity of a scintillation event is to compare the total energy of the scintillation event against an energy "window" or range of expected energies for valid (i.e., unscattered) events. In order to obtain the total energy of the event, light pulse detection voltage signals generated from each photosensor device as a result of a single gamma interaction must be accurately integrated from the start of each pulse, and then added together to form an energy signal associated with a particular event. Energy signals falling within the predetermined energy window are considered to correspond to valid events, while energy signals falling outside of the energy window are considered to correspond to scattered, or invalid, events, and the associated event is consequently not used in the construction of the radiation image, but is discarded.

Another instance of inaccurate information may arise when two gamma photons interact with the scintillation crystal within a time interval that is shorter than the time resolution of the system (in other words the amount of time required for a light event to decay sufficiently such that the system can process a subsequent light event as an independent event), such that light events from the two gamma interactions are said to "pile up," or be superposed on each other. The signal resulting from a pulse pile-up would be meaningless, as it would not be possible to know whether the pulse resulted from two valid events, two invalid events, or one valid event and one invalid event.

More specifically, when a gamma photon interacts with the detector of a nuclear medical imaging system, it causes an electrical output pulse to be produced that rises relatively quickly and then decays from its peak value exponentially. The rise time of the pulse is constrained mainly by the design of the camera electronics, while the exponential decay time is dependent on the detector material. For a conventional NaI scintillation crystal detector material, the decay time constant is on the order of 0.25 microseconds. After the expiration of about 4 time constants (i.e. about 1 microsecond), the output pulse for detection and processing purposes is gone, such that the system is ready to detect a new gamma interaction event.

In actuality, however, the "tail" of the output pulse exists for a much longer time as defined by a second decay time constant, but with a peak value that is so small that it is not detectable. Where there are many gamma interactions in a period of time that is short as compared with the longer decay time constant, the values of the pulse tails of such interactions are added together in the detector, thereby producing a DC shift of the detector output signal.

The value of a gamma interaction event is determined by integrating the pulse signal produced by a single gamma photon for about 1 microsecond (i.e., four decay time constants), over all photomultiplier tubes coupled to the scintillation crystal. That is, the signals produced by all photomultipliers are summed together in order to obtain a measure of the total energy of the event. This summed signal can be called Esum, which is proportional to the energy of the incident gamma that interacted with the scintillation crystal. Where there are many gamma interactions in a period of time that is short as compared with the longer decay time constant, the accumulated value of the slowly decaying tails of many prior events gets added to the integrated value of the current event being processed, and therefore produces an error in the integrated value of the event. This is known as pre-pulse pile-up.

Different solutions to the pulse pile-up problem are known in the prior art. One such solution involves the use of pile-up rejection circuitry, which either precludes the detector from processing any new pulses before processing has been completed on a prior pulse, or stops all processing when a pile-up condition has been identified. This technique addresses the problem of post-pulse pile-up, wherein a subsequent pulse occurs before processing of a pulse of interest is completed. Such rejection circuitry, however, may undesirably increase the "deadtime" of the imaging system, during which valid gamma events are being received but are not able to be processed, thereby undesirably increasing the amount of time needed to complete an imaging procedure.

Another known technique addresses the problem of pre-pulse pile-up, wherein a pulse of interest is overlapped by the trailing edge or tail of a preceding pulse or pulses as described above. This technique uses an approximation of the preceding pulse tail to correct the subsequent pulse of interest. Such approximation is less than optimal because it is not accurate over the entire possible range of pile-up conditions. Further, it requires knowledge as to the precise time of occurrence of the preceding pulse, which is difficult to obtain using analog signals. Additionally, this technique consumes a large amount of computational capacity.

DC-offset correction is also known, for example, from U.S. Pat. No. 5,847,395, incorporated herein by reference in its entirety. The '395 patent discloses the use of a flash analog-to-digital converter (FADC) associated with each photosensor device (e.g., photomultiplier tube (PMT)), and a data processor that integrates the FADC output signals, generates a fraction of a running sum of output signals, and subtracts the fraction from the integrated output signals to generate an adjustment signal to correct the output signals for baseline drifts. However, this solution does not accurately compensate for baseline shifts caused by accumulation of afterglow signals or slow decay pulse tails.

The '395 patent discloses two methods of baseline correction: for relatively slow time scale drift errors caused by electronics, a digital-to-analog converter (DAC) is used to generate pseudo-event signals that are applied to the FADC; the resultant output of the FADC is applied to an integration correction processor to generate an integration adjustment signal that is subtracted from actual event signals from the FADC. For relatively fast time scale drift errors, when the detector is not viewing light generated by incident gammas or X-rays, the FADC is strobed during time intervals between real events, so as to sample the zero baseline signal. A running average of the sampled baseline is maintained over a predefined number of samples, and this average is used to generate a correction signal COR that is then subtracted from the actual event output signals produced by the FADC. Neither of these methods takes into account actual baseline drifts caused by accumulation of gamma event afterglow.

Therefore, there exists a need in the art for a solution that improves the elimination of inaccuracies in event pulse value caused by pulse pile-up.

SUMMARY OF THE INVENTION

The present invention solves the existing need according to a first aspect by providing a method of calibrating a nuclear medical imaging apparatus for effects of scintillation pulse afterglow, including the steps of determining a minimum value of an Esum output signal of the apparatus in response to a relatively low count rate radiation source; determining a minimum value of an Esum output signal of the apparatus in response to a relatively high count rate radiation source; c) comparing the minimum value of the high count rate Esum output signal with the minimum value of the low count rate Esum output signal; d) incrementing an afterglow correction value used to correct the Esum output signal if the minimum value of the high count rate Esum output signal is greater than the minimum value of the low count rate Esum output signal, and repeating steps a)-c) using the incremented afterglow correction value; and e) storing a present value of the afterglow correction value as a calibrated correction value if the minimum value of the high count rate Esum output signal is not greater than the minimum value of the low count rate Esum signal.

According to another aspect of the invention, a method is provided for correcting an Esum output signal of a nuclear medical imaging apparatus, which includes storing a sample series of the Esum output signal obtained at a first sampling rate; detecting a scintillation event using a sample of the Esum output signal obtained at a second sampling rate; determining a minimum value of the Esum output signal from the stored sample series upon detection of a scintillation event; using the determined minimum value to obtain a first DC shift correction value;

mathematically operating on the first DC shift correction value with a second DC shift correction value obtained by calibrating a scintillation detector of the nuclear medical imaging apparatus using two radiation sources of differing count rates, to obtain a third DC shift correction value; and correcting the Esum output signal for DC offset by using the third DC shift correction value.

According to yet another aspect of the invention, a nuclear medical imaging apparatus is provided, which includes a scintillation detector that interacts with radiation photons to produce light events, and produces signals corresponding to the light events; a first analog-to-digital converter (ADC) that receives the signals, samples the received signals and outputs Esum signals; and a DC shift correction circuit that corrects the Esum output signals of the ADC using a DC shift correction signal obtained by a mathematical combination of a first DC shift correction value obtained by determining a minimum value of the Esum output signal prior to the detection of a light event, with a second DC shift correction value obtained by calibrating the scintillation detector of the nuclear medical imaging apparatus using two radiation sources of differing count rates.

BRIEF DESCRIPTION OF THE DRAWINGS

The invention will become more clearly understood from the following detailed description in connection with the accompanying drawings, in which.

DETAILED DESCRIPTION OF THE PREFERRED EMBODIMENTS

Figure 1:
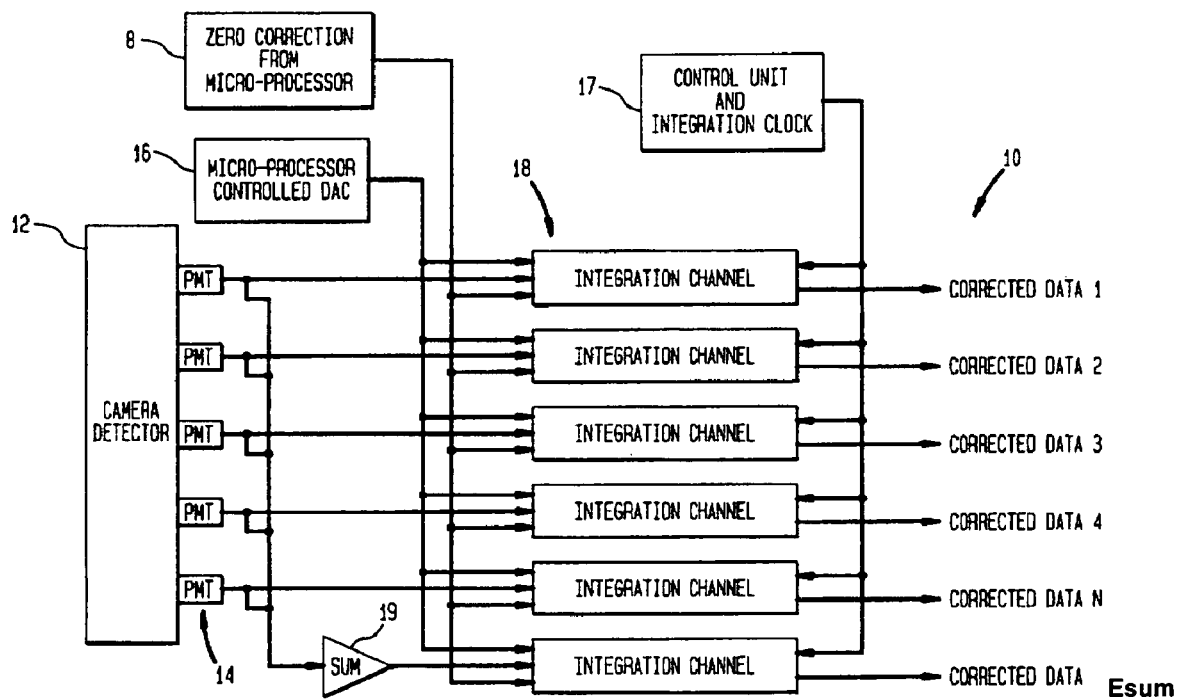
FIG. 1 is a block diagram of an adaptive baseline correction circuit for a nuclear medicine imaging system according to the prior art.

Referring to FIG. 1, a medical imaging system 10 according to the prior art, as disclosed in the aforementioned '395 patent, produces signals corresponding to events detected by a sensor such as a scintillation crystal camera detector 12. Upon absorption of incident gamma rays in the detector 12, corresponding scintillation light events are amplified by a plurality of photodetectors such as PMTs (photomultiplier tubes) 14 forming a two-dimensional array on the scintillation crystal of the detector 12. Each PMT corresponds to a respective channel, the signals from which are processed together with signals from the other channels, to calculate the spatial location of a gamma event occurring in the scintillation crystal.

The signals from the plurality of PMT channels are processed by a plurality of integration channel processing units 18 incorporating signal processing circuitry, with each processing unit 18 being operatively connected to a corresponding one of PMTs 14 for dedicated adjustment of baseline signals from each corresponding PMT.

A zero correction signal 8 is generated from a microprocessor (not shown), and a microprocessor controlled digital-to-analog converter (DAC) 16 generates pseudo-event signals. Adder 19 generates a running sum of the data signals from all of the PMTs 14, to produce an energy signal that corresponds to the total energy of a scintillation event. In response to control and clock signals from a control unit and integration clock circuit 17, the processing units 18 process the zero correction signals 8, the pseudo-event signals from DAC 16, and the amplified signals from the PMTs 14 using associated integration channels to generate corrected data signals for each channel i=1 . . . N. The sum from the adder 19 is outputted as data signal E.

The calibration of the zero correction signals applied to the integration channel processing units 18 is as follows. For physical phenomena having characteristic times which are short compared to an image acquisition, but still much longer than that of a gamma ray event, such as the afterglow of the crystal, for each PMT 14 the average DC output value is updated prior to a current event $T_0$ and is then subtracted from the sensor output that is responsive to event $T_0$ to yield a corrected output value.

Phenomena which vary slowly in time, such as DC amplifier drift, are measured when the camera 12 is not actively detecting actual events. In this case the response of the integration channel processing unit 18 to simulated event signals generated by DAC 16 is measured. The measured response to such pseudo-events is used to calculate the baseline offset value for adjustment prior to detection of an actual event. In operation, the slow phenomena and fast phenomena zero correction signals are combined such as by addition, and the combined zero correction signal is then subtracted from the PMT output signals to produce a final output signal.

According to the present invention, a DC offset correction value is obtained that accurately compensates for DC shifts caused by actual gamma event afterglow in the scintillation crystal of the imaging detector. The DC offset correction value is obtained by generating a static afterglow correction value AGS that is calibrated to the scintillation crystal, and a dynamic afterglow correction value AGM that is proportional to the zero offset of the sensor circuitry as measured just prior to the occurrence of a scintillation event. The static value AGS is then multiplied by the dynamic value AGM, to produce a DC offset correction signal AGC.

Figure 2:
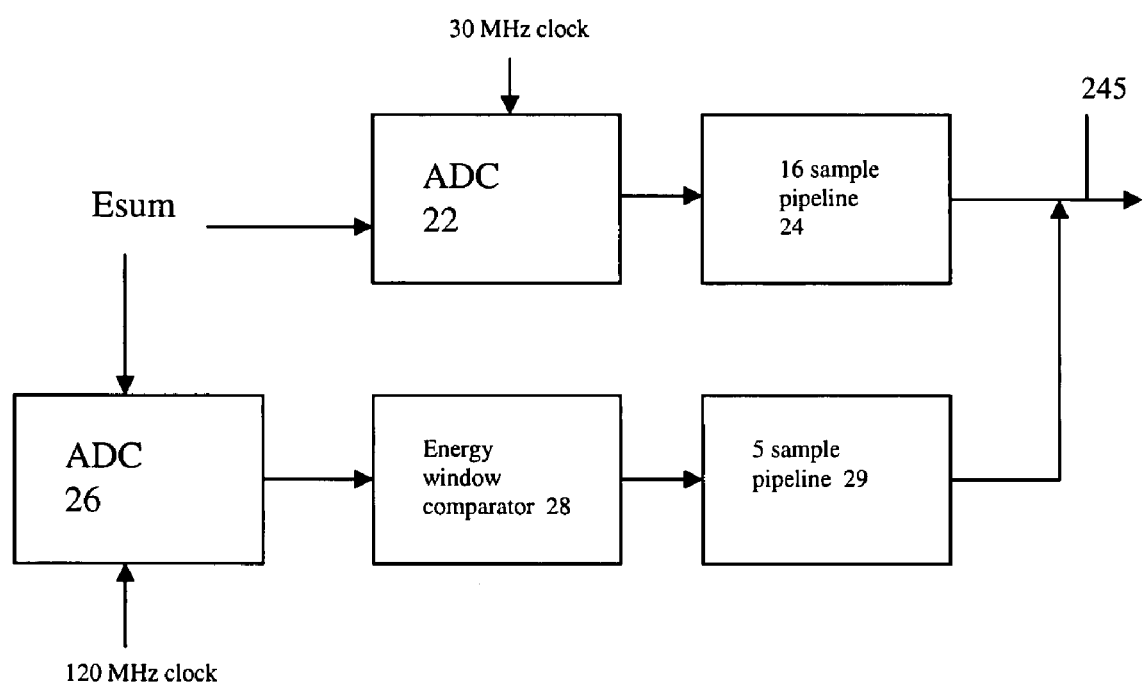
FIG. 2 is a block diagram of a system for determining a zero value of an Esum output signal, in accordance with the concepts of the present invention.

FIG. 2 illustrates a circuit for determining the zero value at the Esum output. This determination is made for each detected event (or for each of a group of successive events), and therefore is a dynamic correction. The Esum signal (i.e., from the output of summing amplifier 19 of FIG. 1) is fed to a first analog-to-digital converter ADC 22, which runs at a clock speed of 30 MHz and includes a 16 sample pipeline register 24. The Esum signal also is fed to a second ADC 26, which runs at a clock speed of 120 MHz (i.e., four times faster than ADC 22) and includes a 5 sample pipeline register 29. The output of ADC 26 is fed to an energy window comparator 28 as is well known in the art, which compares the value of the ADC 26 output signal with upper and lower energy values that define a "window" within which a true scintillation event is determined.

Upon detection of a true scintillation event by the comparator 28, the sample data being outputted by the 16 sample pipeline register 24 corresponds to about 10 clock cycles prior to the start of the event. The zero value of the Esum signal is then found by observing the output of the ADC 22 on output signal line 245 to find its minimum value after the detection of a true event by the comparator 28. The minimum value so determined corresponds to a dynamic afterglow zero correction value AGM. This value then is stored in memory.

In accordance with the present invention, an afterglow calibration of the scintillation detector is carried out to obtain a correction value AGS that corresponds to the DC shift caused by gamma afterglow in the scintillation crystal. This calibration process may be performed prior to a clinical imaging procedure, or less frequently such as once per day, once per week, etc. Consequently, this calibration process produces a static afterglow zero correction value AGS.

Figure 3:
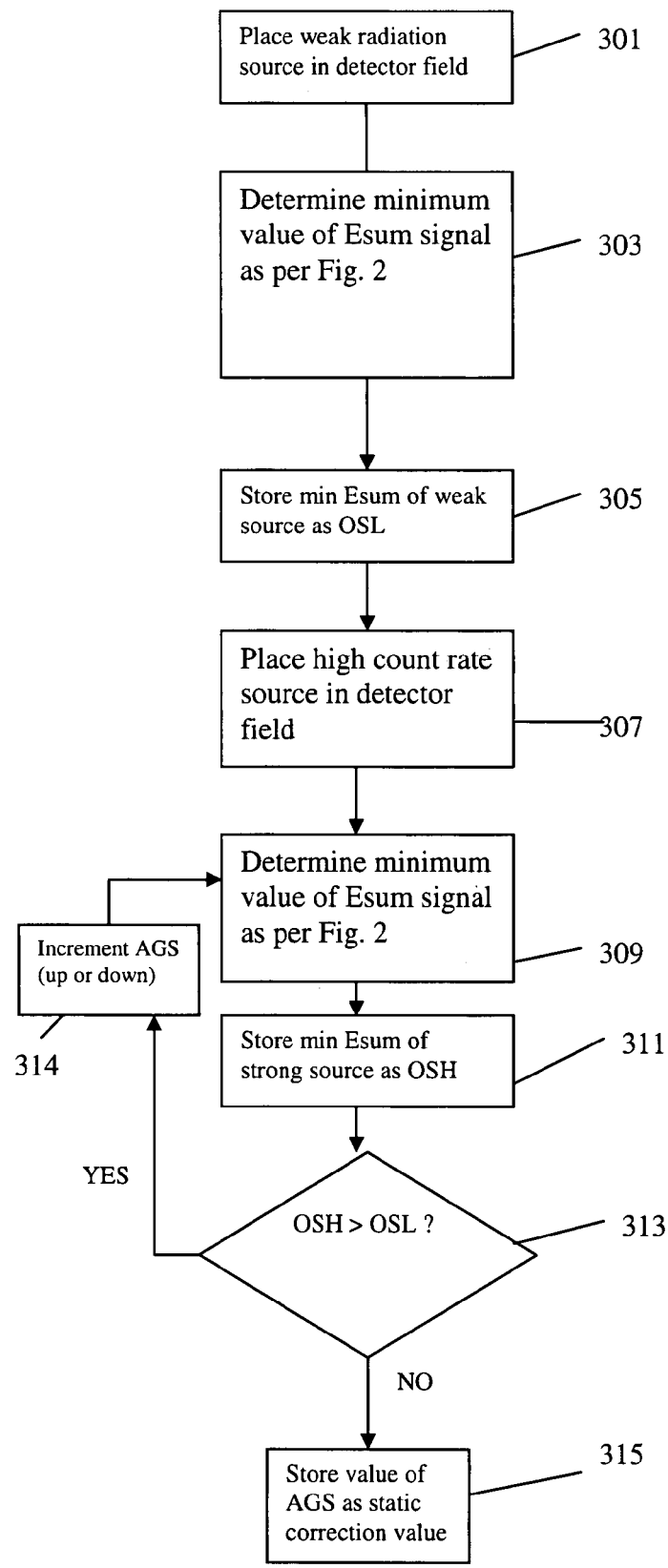
FIG. 3 is a flow diagram of a scintillation detector afterglow calibration process according to an embodiment of the present invention.

Referring now to FIG. 3, an afterglow calibration method according to a preferred embodiment of the invention will be described. At step 301, a weak (i.e., low count rate) radiation source is placed within the detection field of the imaging detector of the system. The count rate of the weak source is such that no dc shift of the Esum output of the ADC 22 is produced because of afterglow, as the time spacing between successive events is greater than the detectable decay of a scintillation pulse tail.

At step 303, the minimum value of the Esum output signal is found, similar to the process carried out in FIG. 2. In the method of FIG. 3, however, a digital filter may be used to process the measured values so as to generate an average value for the Esum minimum. The Esum zero value then is stored as a parameter OSL (i.e., zero static low value) at step 305.

Next, at step 307 the weak radiation source is removed and replaced with a high count radiation source. The high count rate source is selected so that gamma event afterglow will have a significant DC shift effect on Esum. At step 309 the minimum value of the Esum output of the ADC 22 in response to the high count rate source is determined. This Esum zero value then is stored as a parameter OSH (i.e., zero static high value) at step 311.

At step 313, the stored value of OSH is compared with the stored value of OSL. If the stored value of OSH is greater than the stored value of OSL, this means that the detector is not properly calibrated to correct for afterglow DC shifts in the Esum signal. Accordingly, the value of the static afterglow zero correction value AGS is incremented at step 314 (either increased or decreased as appropriate). It is noted that at the beginning of a calibration process, the value of AGS may be set to zero or to a very small correction value, which then may incremented by predefined increments as the calibration process is progressed. Further, the change to the static correction value AGS may be digitally filtered to reduce or cancel out statistical noise that may be present in the calibration process.

As indicated in FIG. 3, the process then returns to step 309, where the process is again performed with the high count rate radiation source, but where the Esum output signal is corrected using the updated value of AGS. Calibration process iterations will continue to be performed, until such time that the current stored value of parameter OSH is the same as the current stored value of parameter OSL. This condition indicates that the current value of AGS represents a proper calibration of the scintillation detector to cancel out DC shift caused by scintillation pulse afterglow. Consequently, the process then advances to step 315 where the current value of AGS is stored as the static correction value to be used in actual clinical imaging.

During actual clinical imaging, the dynamic correction value AGM is multiplied by the static correction value AGS so as to obtain a DC offset correction value AGC, which is subtracted from the Esum output of the ADC, in order to obtain an accurate Esum signal that is free of afterglow and other causes of DC shift. This can be notated as:

$$AGC = AGM * AGS$$

$$ADC_{corrected} = ADC_{output} - AGC$$

The invention having been thus described, it will be apparent to those of skill in the art that the same may be varied in many ways without departing from the spirit and scope of the invention. Any and all such variations as would be apparent to those skilled in the art are intended to be covered by the following claims.

What is claimed is:

1. A method of calibrating a nuclear medical imaging apparatus for effects of scintillation pulse afterglow, comprising the steps of:
    a) determining a minimum value of an Esum output signal of said apparatus in response to a relatively low count rate radiation source;
    b) determining a minimum value of an Esum output signal of said apparatus in response to a relatively high count rate radiation source;
    c) comparing the minimum value of the high count rate Esum output signal with the minimum value of the low count rate Esum output signal;
    d) incrementing an afterglow correction value used to correct said Esum output signal if the minimum value of the high count rate Esum output signal is greater than the minimum value of the low count rate Esum output signal, and repeating steps a)-c) using the incremented afterglow correction value; and
    e) storing a present value of said afterglow correction value as a calibrated correction value if the minimum value of the high count rate Esum output signal is not greater than the minimum value of the low count rate Esum signal.

2. The method of claim 1, further comprising the step of processing an Esum output signal using a digital filter, to generate an average minimum value of said Esum output signal.

3. The method of claim 1, further comprising the step of digitally filtering indicated increments to said afterglow correction value to reduce any statistical noise introduced by the calibration process.

4. The method of claim 1, wherein said afterglow correction value is used to subtract a DC offset from said Esum output signal.

* * * * *